US009835821B1

(12) United States Patent
Yin et al.

(10) Patent No.: US 9,835,821 B1
(45) Date of Patent: Dec. 5, 2017

(54) FIVE-SURFACE WIDE FIELD-OF-VIEW COMPOUND LENS AND ASSOCIATED CAMERA MODULE

(71) Applicant: OmniVision Technologies, Inc., Santa Clara, CA (US)

(72) Inventors: Chuen-Yi Yin, New Taipei (TW); Jau-Jan Deng, Taipei (TW)

(73) Assignee: OmniVision Technologies, Inc., Santa Clara, CA (US)

( * ) Notice: Subject to any disclaimer, the term of this patent is extended or adjusted under 35 U.S.C. 154(b) by 0 days.

(21) Appl. No.: 15/220,061

(22) Filed: Jul. 26, 2016

(51) Int. Cl.
G02B 23/24 (2006.01)
G02B 9/60 (2006.01)
G02B 9/12 (2006.01)
G02B 13/00 (2006.01)
G03B 17/08 (2006.01)
G02B 27/00 (2006.01)
A61B 1/00 (2006.01)
A61B 1/05 (2006.01)

(52) U.S. Cl.
CPC ............ *G02B 9/60* (2013.01); *A61B 1/00163* (2013.01); *A61B 1/05* (2013.01); *G02B 9/12* (2013.01); *G02B 13/0035* (2013.01); *G02B 13/0045* (2013.01); *G02B 13/0085* (2013.01); *G02B 23/243* (2013.01); *G02B 27/0025* (2013.01); *G03B 17/08* (2013.01)

(58) Field of Classification Search
None
See application file for complete search history.

(56) References Cited

U.S. PATENT DOCUMENTS

2014/0018613 A1 1/2014 Scott et al.
2014/0334016 A1* 11/2014 Yin .................... G02B 13/0085
359/714

* cited by examiner

*Primary Examiner* — Darryl J Collins
(74) *Attorney, Agent, or Firm* — Lathrop Gage LLP

(57) ABSTRACT

A five-surface wide field-of view compound lens incudes a first lens, a second lens, a third lens, a fourth lens, a fifth lens, a first biplanar substrate, and a second biplanar substrate. The first lens is plano-concave; the second, the third lens, and the fourth lens are plano-convex; the fifth lens is a plano-gull-wing lens. The first biplanar substrate is between the second lens and the third lens. The second biplanar substrate is between the fourth lens and the fifth lens. The first lens has a first Abbe number. The second lens has a second Abbe number less than the first Abbe number. A camera module includes the five-surface wide FOV compound lens and a glass substrate having a planar surface adjoining a first planar surface of the first lens, the first lens being between the glass substrate and the second lens.

22 Claims, 15 Drawing Sheets

| surface | radius $r_c$ (mm) | thickness (mm) | $n_d$ (λ=587.3 nm) | Abbe number | conic $k$ | aspheric coefficient | | | | |
|---|---|---|---|---|---|---|---|---|---|---|
| | | | | | | 4th-order term $\alpha_4$ | 6th-order term $\alpha_6$ | 8th-order term $\alpha_8$ | 10th-order term $\alpha_{10}$ | 12th-order term $\alpha_{12}$ |
| 261F | ∞ | 0.4000 | 1.5170 | 63.00 | 0 | 0 | 0 | 0 | 0 | 0 |
| 211(1) | ∞ | 0.0200 | 1.5110 | 57.00 | 0 | 0 | 0 | 0 | 0 | 0 |
| 212(1) | 0.2554 | 0.2723 | 1.0 | -- | -0.9365 | -2.2462 | -2.6201 | -13.7479 | 38.6011 | 52.4169 |
| 221(1) | 0.4111 | 0.2007 | 1.5900 | 31.00 | -1.9542 | 0.9686 | -11.0028 | 9.5366 | 30.1862 | 54.2761 |
| 222(1) | ∞ | 0.0000 | 1.0 | -- | 0 | 0 | 0 | 0 | 0 | 0 |
| 262(1)F | ∞ | 0.3050 | 1.5170 | 63.00 | 0 | 0 | 0 | 0 | 0 | 0 |
| 263(1)F | ∞ | 0.2500 | 1.5170 | 63.00 | 0 | 0 | 0 | 0 | 0 | 0 |
| 231(1) | ∞ | 0.0754 | 1.5110 | -- | 0 | 0 | 0 | 0 | 0 | 0 |
| 232(1) | -4.9245 | 0.0671 | 1.0 | -- | 0 | -9.2979 | 94.8273 | -498.5575 | 1217.8544 | -1194.2791 |
| 241(1) | 0.4513 | 0.1226 | 1.5110 | 57.00 | -8.9181 | -0.0544 | -2.9081 | -9.2483 | 112.8475 | -233.9060 |
| 242(1) | ∞ | 0.0000 | 1.0 | -- | 0 | 0 | 0 | 0 | 0 | 0 |
| 264(1)F | ∞ | 0.3000 | 1.5170 | 63.00 | 0 | 0 | 0 | 0 | 0 | 0 |
| 251(1) | ∞ | 0.0200 | 1.5200 | 50.00 | 0 | 0 | 0 | 0 | 0 | 0 |
| 252(1) | -9.7369 | 0.1341 | 1.0 | -- | -104.2760 | 2.5179 | -10.8669 | 16.4206 | -4.9654 | -7.6693 |
| 265F | ∞ | 0.4000 | 1.5170 | 63.00 | 0 | 0 | 0 | 0 | 0 | 0 |
| 265B | ∞ | 0.0450 | 1.0 | -- | 0 | 0 | 0 | 0 | 0 | 0 |

FIG. 4

FIVE-SURFACE WIDE FIELD-OF-VIEW COMPOUND LENS AND ASSOCIATED CAMERA MODULE

BACKGROUND

Digital camera modules are used in a variety of consumer, industrial, and scientific imaging devices to produce still images and/or video. One such imaging device is a video endoscope, a medical diagnostic instrument used for imaging a ventricle within a patient. It includes a flexible shaft capable of being inserted into the patient through an orifice thereof. The shaft has a tip that includes a light source and a camera for respectively illuminating and capturing images of part of the patient, such as a body cavity or an organ. The endoscope has a field of view by virtue of the imaging lens and image sensor of its camera module. The camera module preferably has a wide field of view (FOV) and produce quality images while being sufficiently small to enable endoscope access to small ventricles of a patient.

Conventional compact wide-FOV camera modules are formed of molded glass. A disadvantage of such camera modules is their cost, as conventional processes of molding glass lenses is not compatible with high-volume production methods.

SUMMARY OF THE INVENTION

In a first embodiment, a five-surface wide FOV compound lens incudes a first lens, a second lens, a third lens, a fourth lens, a fifth lens, a first biplanar substrate, and a second biplanar substrate. The first lens is plano-concave; the second, the third lens, and the fourth lens are plano-convex; the fifth lens is a plano-gull-wing lens. The first biplanar substrate is between the second lens and the third lens. The second biplanar substrate is between the fourth lens and the fifth lens. The Abbe number of the first lens is greater than the Abbe number of the second lens.

In a second embodiment, a five-surface wide FOV compound lens includes a first lens, a second lens, a third lens, a fourth lens, a fifth lens, a first biplanar substrate, and a second biplanar substrate. The first lens is plano-concave; the second, the third lens, and the fourth lens are plano-convex; the fifth lens is a plano-gull-wing lens. The first biplanar substrate is between the second lens and the third lens. The second biplanar substrate is between the fourth lens and the fifth lens. The Abbe number of the first lens is greater than the Abbe number of the second lens. The second lens has a focal length $F_2$, and the fourth lens has a focal length $F_4$, wherein the ratio $F_2/F_4$ satisfies $0.65<F_2/F_4<0.95$.

In a third embodiment, a camera module includes the five-surface wide FOV compound lens of either the first or second embodiment, and a glass substrate having a planar surface adjoining a first planar surface of the first lens, the first lens being between the top substrate and the second lens.

BRIEF DESCRIPTION OF THE FIGURES

FIG. 4 shows a table of exemplary parameters of the compound lens of FIG. 3.

DETAILED DESCRIPTION

Figure 1:
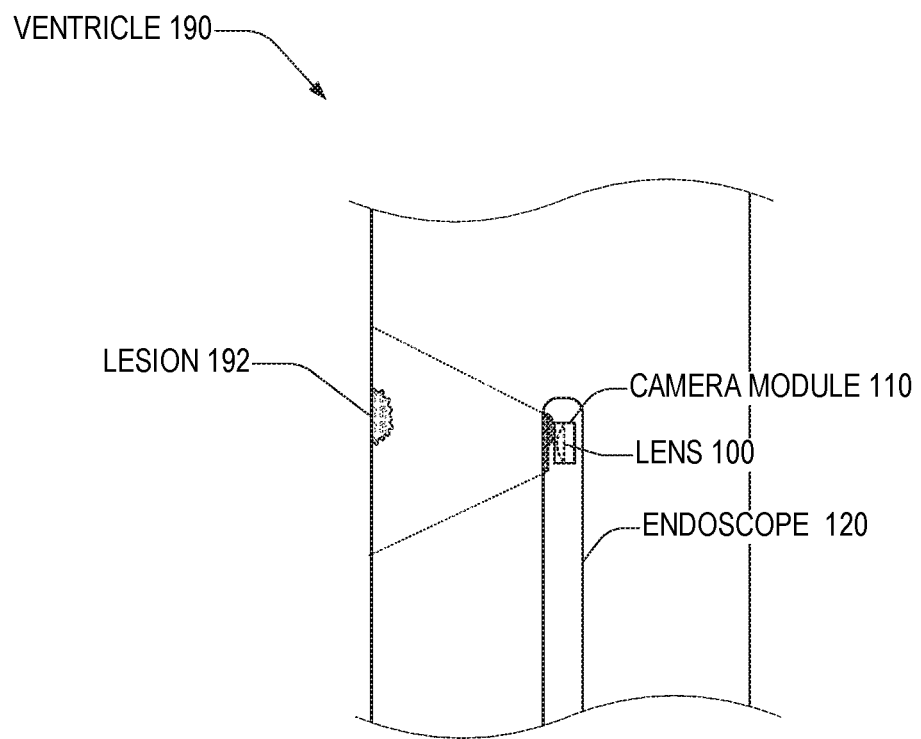
FIG. 1 illustrates a five-surface wide FOV compound lens in a use scenario, according to an embodiment.

FIG. 1 is a cross-sectional view of a ventricle 190 that includes a lesion 192 imaged by a video endoscope 120 that includes a camera module 110 having an five-surface wide FOV compound lens 100.

Figure 2:
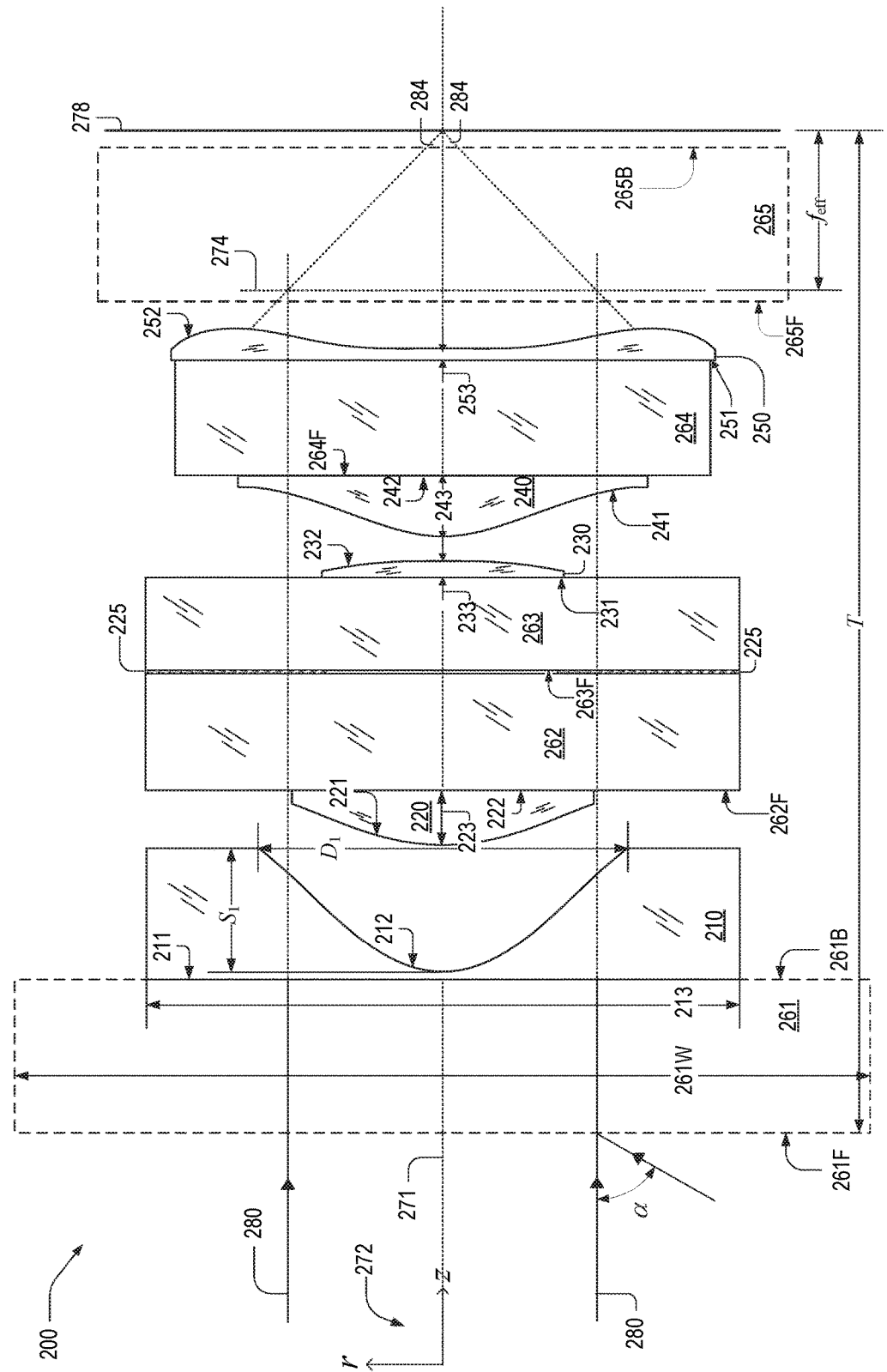
FIG. 2 is a cross-sectional view of an embodiment of the five-surface wide FOV compound lens of FIG. 1.

FIG. 2 is a cross-sectional view of a five-surface wide FOV compound lens 200, which is an embodiment of five-surface wide FOV compound lens 100 of FIG. 1. Compound lens 200 includes biplanar substrates 262-264, a first lens 210, a second lens 220, a third lens 230, a fourth lens 240, and a fifth lens 250. Lens 210 has a planar surface 211 and a concave surface 212. Lenses 220, 230, and 240 have respective planar surfaces 222, 231, and 242 and respective convex surfaces 221, 232, and 241. Lenses 220, 230, 240, and 250 have respective center thicknesses 223, 233, 243, and 253. Substrates 262, 263, and 264 have respective front surfaces 262F, 263F, and 264F.

First lens 210 is a negative lens and second lens 220, third lens 230, and fourth lens 240 are each positive lenses. Lens 250 has a planar surface 251 and a gull-wing surface 252 that includes both convex and concave regions. Accordingly, lens 250 is an example of a "plano-gull-wing lens." The five surfaces referred to by "five-surface wide FOV compound lens" 200 are the non-planar surface of each lens thereof: surfaces 212, 221, 232, 241, and 252.

Compound lens 200 may include a top substrate 261, which has a front surface 261F and a back surface 261B. Both surfaces 261F and 261B may be planar surfaces. Top substrate 261 may have a width 261W that exceeds an outer diameter 213 of lens 210, for example, when compound lens 200 is part of a camera module and at least part of top substrate 261 forms an exterior surface of the camera module. Substrate 261 is for example formed of glass, while lens 210 may be formed of UV-curable epoxy, which is less durable than glass and is unlikely to survive a sterilization process. When compound lens 200 with top substrate 261 is incorporated into a camera module, substrate 261 protects lens 210 and provides the camera module a robust top surface (surface 261F) which, unlike a UV-curable epoxy, can withstand processes of sterilization and also hermetically seal the camera module.

Compound lens 200 also may include a coverglass 265, which has a front surface 265F and a back surface 265B. When included in compound lens 200, cover glass 265 covers a pixel array of an image sensor, not shown, located at image plane 278. The specific type of pixel array and image sensor may vary and is thus not discussed in detail herein. Alternatively, an embodiment of compound lens 200 not including coverglass 265 may be configured to cooperate with a coverglass 265 to image a scene onto an image sensor to which coverglass 265 is bonded Lenses 210, 220, 230, 240, and 250 may have a common optical axis 271. Substrates 262 and 263 may be a single optical element. Without departing from the scope hereof, compound lens 200 may include an optical element between one or more of (i) substrate 262 and lens 220, (ii) substrate 263 and lens 230, (iii) substrate 264 and lens 240, and (iv) substrate 264 and lens 250.

Lenses 210, 220, 230, 240, and 250 may be formed of a solder-reflow compatible material via a wafer-level optics replication process. A solder-reflow compatible material for example withstands surface-mount technology (SMT) reflow soldering processes occurring at temperatures exceeding 250° C., such that a camera module, including compound lens 200 and an image sensor coupled therewith, may be surface-mounted to a circuit board via a solder-reflow process. Lenses 210, 220, 230, 240, and 250 may also be formed via injection molding or other methods known in the art. Alternatively, lenses 210, 220, 230, 240, and 250 may be formed from glass via precision glass molding (also known as ultra-precision glass pressing) or other methods known in the art.

At least one of lenses 210, 220, 230, 240, and 250 may be a singlet lens. At least one of lenses 210, 220, 230, 240, and 250 may be a non-singlet lens without departing from the scope hereof. At least one of surfaces 212, 221, 232, 241, and 252 may be an aspheric surface. At least one of surfaces 212, 221, 232, and 241 may be a spherical surface without departing from the scope hereof.

Second lens 220 has a focal length $F_2$ and fourth lens 240 has a focal length $F_4$. An embodiment of compound lens 200 has a quotient $F_2/F_4$ between 0.65 and 0.95. Third lens 230 has a focal length $F_3$ and fifth lens 250 has a focal length $F_5$. An embodiment of compound lens 200 has a quotient $F_3/F_5$ satisfying $0.2 < |F_3/F_5| < 0.6$.

Limiting quotient $F_2/F_4$ and $|F_3/F_5|$ to the aforementioned ranges balances aberrations, such as astigmatism and distortion, in an image formed by compound lens 200 such that compound lens 200 is capable of forming images of sufficient quality to meet the goals of an endoscopy procedure.

First lens 210, second lens 220, third lens 230, fourth lens 240, and fifth lens 250 are formed of materials having, respectively, a first Abbe number $V_1$, a second Abbe number $V_2$, a third Abbe number $V_3$, a fourth Abbe number $V_4$, and a fifth Abbe number $V_5$. Herein, all refractive index values and middle wavelength of Abbe numbers correspond to $\lambda_d$=587.6 nm unless otherwise specified. In compound lens 200, Abbe number $V_1$ may each exceed Abbe number $V_2$. In one example, Abbe number $V_1$ exceeds 48 and Abbe number $V_2$ is less than 35. These constraints on Abbe numbers allow for limiting chromatic aberration in images formed by compound lens 200.

Transparent optical materials with $V_d>48$ include polymethyl methacrylate (PMMA), alicyclic acrylate (e.g., Optrez OZ1230(1)®), and cycloolefin polymers (e.g., APEL™ 5014DP, TOPAS® 5013, ZEONEX® 480R, and Arton FX4727). A lens material with $V_d>48$ may be plastic or non-plastic optical material, such as glass, without departing from the scope hereof.

Transparent optical materials with $V_d<35$ include PAN-LITE® (a brand-name polycarbonate), Udel® P-1700 (a brand-name polysulfone), and OKP-4 (a brand-name optical polyester). A lens material with $V_d<35$ may be plastic or a non-plastic optical material, such as glass, without departing from the scope hereof.

FIG. 2 shows compound lens 200 focusing parallel rays 280 onto an image plane 278. Converging rays 284 exit compound lens 200 at surface 252 of lens 250 and converge at image plane 278. Extensions of rays 280 and 284 into compound lens 200 intersect at a principal plane 274. FIG. 2 shows principal plane 274 intersecting optical axis 271 between lens 250 and image plane 278 for illustrative purposes only. Principal plane 274 may intersect optical axis 271 at different locations without departing from the scope hereof.

Compound lens 200 may include an aperture stop 225 between lenses 220 and 230. Aperture stop 225 is, for example, an opaque coating between substrates 262 and 263. Including two substrates 262 and 263 between lenses 220 and 230 enables positioning of aperture stop 225 in compound lens 200 to maximize symmetry of compound lens 200 about the aperture stop plane, which, per the symmetric principle known in lens design, minimizes aberrations such as coma, distortion, and lateral color.

Compound lens 200 has a FOV 2α, which corresponds to two times a maximum angle α of an incident ray on its front surface with respect to optical axis 271 that propagates through aperture stop 225 and reaches image plane 278. The front surface is for example surface 261F or surface 211.

Compound lens 200 has an effective focal length $f_{eff}$, between principal plane 274 and image plane 278. Compound lens 200 has a total track length T between front surface 261F and image plane 278. Embodiments of compound lens 200 may have a quotient $T/f_{eff}$ between 5.0 and 5.8. Limiting the quotient $T/f_{eff}$ to greater than 5.0 enables compound lens 200 to have a wide field of view. Limiting the quotient $T/f_{eff}$ to less than 5.8 limits the length of compound lens 200.

First lens 210 has a diameter $D_1$, and a sag $S_1$. Embodiments of compound lens 200 may have a quotient $D_1/S_1$ between 2.5 and 3.2. The lower limit of $D_1/S_1$ enables compound lens 200 to have a wide field of view, while the upper limit ensures that lens 210 has dimensions attainable by wafer-level lens manufacturing processes.

Five-Surface Wide Field-of-View Compound Lens, Example 1

Figure 3:
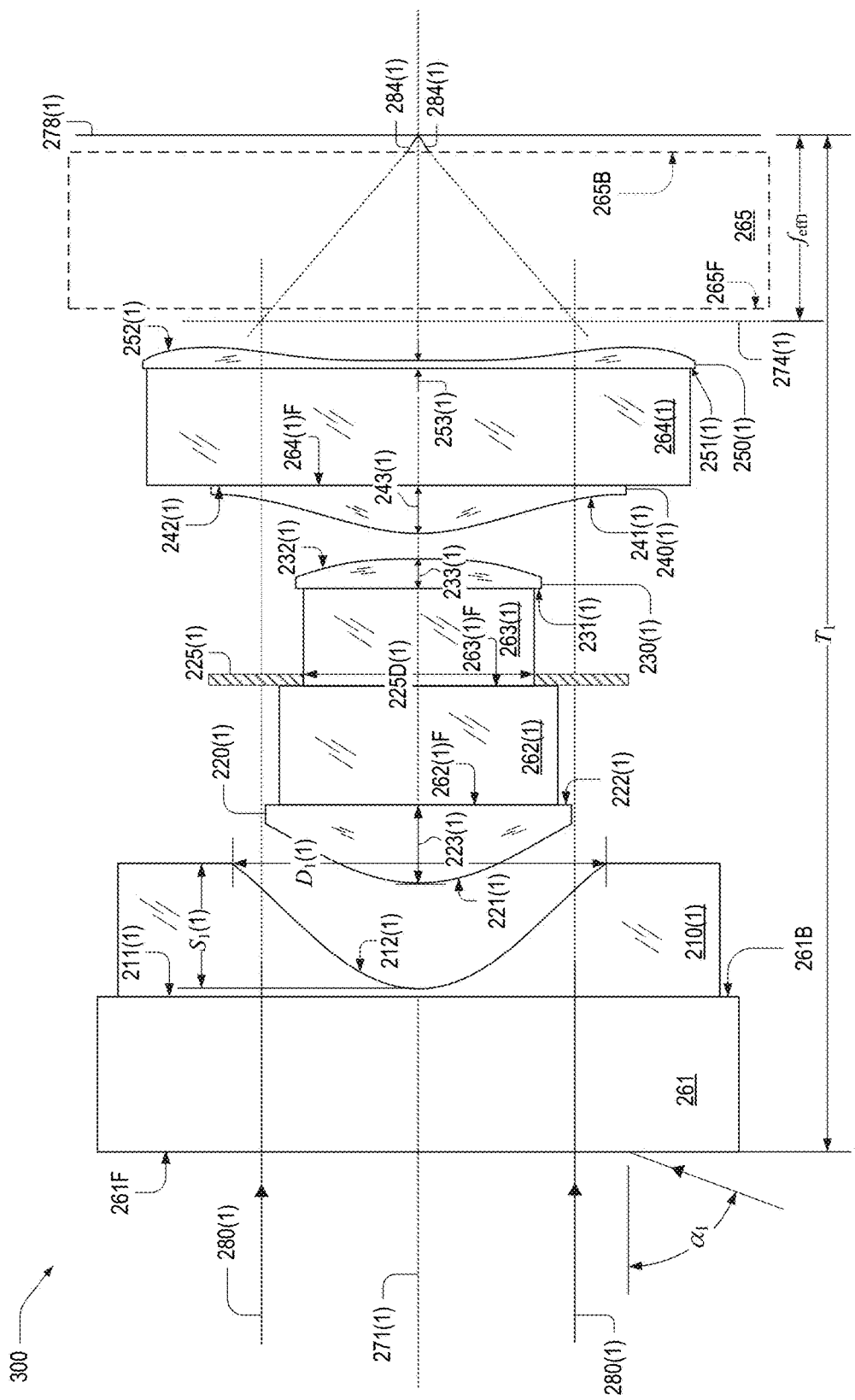
FIG. 3 is a cross-sectional view of an imaging system that includes a first embodiment of the five-surface wide FOV compound lens of FIG. 2.

FIG. 3 is a cross-sectional view of a five-surface wide FOV compound lens 300, which is an embodiment of five-surface wide FOV compound lens 200. Compound lens 300 includes top substrate 261, substrates 262(1)-264(1), a first lens 210(1), a second lens 220(1), an aperture stop 225(1) a third lens 230(1), a fourth lens 240(1), and a fifth lens 250(1). Lenses 210(1), 220(1), 230(1), and 240(1) have respective planar surfaces 211(1), 222(1), 231(1), 242(1) and 251(1) and respective non-planar surfaces 212(1), 221

(1), 232(1), and 241(1). Lens 250(1) has a planar surface 251(1) and a gull-wing surface 252(1). Lenses 210(1), 220(1), 230(1), 240(1), and 250(1) are coaxial with a common optical axis 271(1). Compound lens 300 may also include coverglass 265.

Herein, a figure element denoted by a reference numeral suffixed by a parenthetical numeral indicates an example of the element indicated by the reference numeral. For example, lens 210(1) of FIG. 3 is an example of lens 210 of FIG. 2.

FIG. 4 shows a table 400 of exemplary parameters of each surface of compound lens 300 as well as cover glass 265, with which compound lens 300 is configured to cooperate, or which is included in compound lens 300. Table 400 includes columns 404, 406, 408, 410, 412, and 421-426. Surface column 421 denotes surfaces of top substrate 261, substrates 262(1)-264(1), cover glass 265, lenses 210(1), 220(1), 230(1), 240(1), and 250(1) of FIG. 3.

Column 423 includes center thicknesses of top substrate 261, substrates 262(1)-264(1), cover glass 265, and lenses 210(1), 220(1), 230(1), 240(1), and 250(1). A thickness value in column 423 in a row denoting a specific surface indicates the on-axis distance between that specific surface and the next surface of the row beneath. For example, on optical axis 271(1), surfaces 261F and 211(1) are separated by 0.4000 mm, surfaces 211(1) and 212(1) are separated by 0.0200 mm, and surfaces 212(1) and 221(1) are separated by 0.2723 mm. Surface 265B is 0.045 mm from image plane 278(1). Aperture stop 225(1) has a diameter 225D(1) equal to 0.24 mm.

It should be appreciated that compound lens 300 need not be configured to cooperate with cover glass 265, in which case parameters of compound lens 300 may be reoptimized to form an image at an image plane absent cover glass 265. Likewise, compound lens 300 may be configured to cooperate with a cover glass 265 of thickness or material different from that specified in table 400, in which case parameters of compound lens 300 may be reoptimized accordingly to form an image at an image plane.

Surfaces 211(1), 222(1), 231(1), and 242(1) are defined by surface sag $z_{sag}$, shown in Eqn. 1.

$$z_{sag} = \frac{cr^2}{1 + \sqrt{1 - (1+k)c^2 r^2}} + \sum_{i=1}^{N} \alpha_i r^i \quad (1)$$

In Eqn. 1, $z_{sag}$ is a function of radial coordinate r, where directions z and r are shown in coordinate axes 272, FIG. 2. In Eqn. 1, the parameter c is the reciprocal of the surface radius of curvature $r_C$:

$$c = \frac{1}{r_c}.$$

Column 422 of FIG. 4 lists $r_C$ values for surfaces 212(1), 222(1), 232(1), 241(1), and 252(1). Parameter k denotes the conic constant, shown in column 426. Columns 404, 406, 408, 410, and 412 contain values of aspheric coefficients $\alpha_4$, $\alpha_6$, $\alpha_8$, $\alpha_{10}$, and $\alpha_{12}$ respectively. The units of quantities in table 400 are consistent with $z_{sag}$ in Eqn. 1 being expressed in millimeters.

Column 424 lists values material refractive index $n_d$ at free-space wavelength $\lambda_d$=587.6 nm, and column 425 lists the corresponding Abbe numbers $V_d$. The refractive index and Abbe numbers corresponding to a surface characterize the material between the surface and the surface in the row beneath. For example, the refractive index and Abbe number between surface 261F and 211(1) are 1.517 and 63.00, respectively, and the refractive index and Abbe number between surface 211(1) and 212(1) are 1.511 and 57.00, respectively. Non-dispersive materials have an undefined Abbe number, denoted by "--" in column 425.

Compound lens 300 has a working f-number equal to 3.2 and a field of view $2\alpha_1$=140 degrees. At free-space wavelength $\lambda$=587.6 nm, compound lens 300 has an effective focal length $f_{\it{eff1}}$=0.495 mm between principal plane 274(1) and image plane 278(1).

First lens 210(1) has a $D_1(1)$=0.990, and a sag $S_1(1)$ =0.330 mm, which corresponds to a ratio $D_1(1)/S_1(1)$=3.0. Compound lens 300 has a total track length $T_1$=2.612 mm between surface 261F and image plane 278(1). The ratio of total track length to effective focal length is $T_1/f_{\it{eff1}}$=5.3.

Second lens 220(1) and fourth lens 240(1) have focal lengths $F_2$ and $F_4$ respectively, which may be approximated using the lensmaker's equation. Referring to second lens 220(1), object-side surface 221(1) has a 0.4111-mm radius of curvature, and image-side surface 222(1) is has an infinite radius of curvature. Using these radii of curvature, center thickness 223(1), and $n_d$=1.59, the lensmaker's equation yields $F_2$≈0.70 mm. Referring to fourth lens 240(1), object-side surface 241(1) has a 0.4513-mm radius of curvature, and image-side surface 242(1) has an infinite radius of curvature. Using these radii of curvature, center thickness 243(1), and $n_d$=1.5110, the lensmaker's equation yields $F_4$≈0.88 mm. Ratio $F_2/F_4$ is approximately 0.79.

Third lens 230(1) and fifth lens 250(1) have focal lengths $F_3$ and $F_5$ respectively, which may be approximated using the lensmaker's equation. Referring to third lens 230(1), object-side surface 231(1) has an infinite radius of curvature and image-side surface 232(1) has a −4.9245-mm radius of curvature. Using these radii of curvature, center thickness 233(1), and $n_d$=1.511, the lensmaker's equation yields $F_3$≈9.64 mm. Referring to fifth lens 250(1), object-side surface 251(1) has an infinite radius of curvature and image-side surface 252(1) has a −9.7369-mm radius of curvature. Using these radii of curvature, center thickness 253(1), and $n_d$=1.52, the lensmaker's equation yields $F_5$≈18.73 mm. Ratio |$F_3/F_5$| is approximately 0.52.

FIGS. 5-8 are plots of longitudinal aberration, f-theta distortion, field curvature, and lateral color, respectively, of compound lens 300 as computed by Zemax®.

Figure 5:
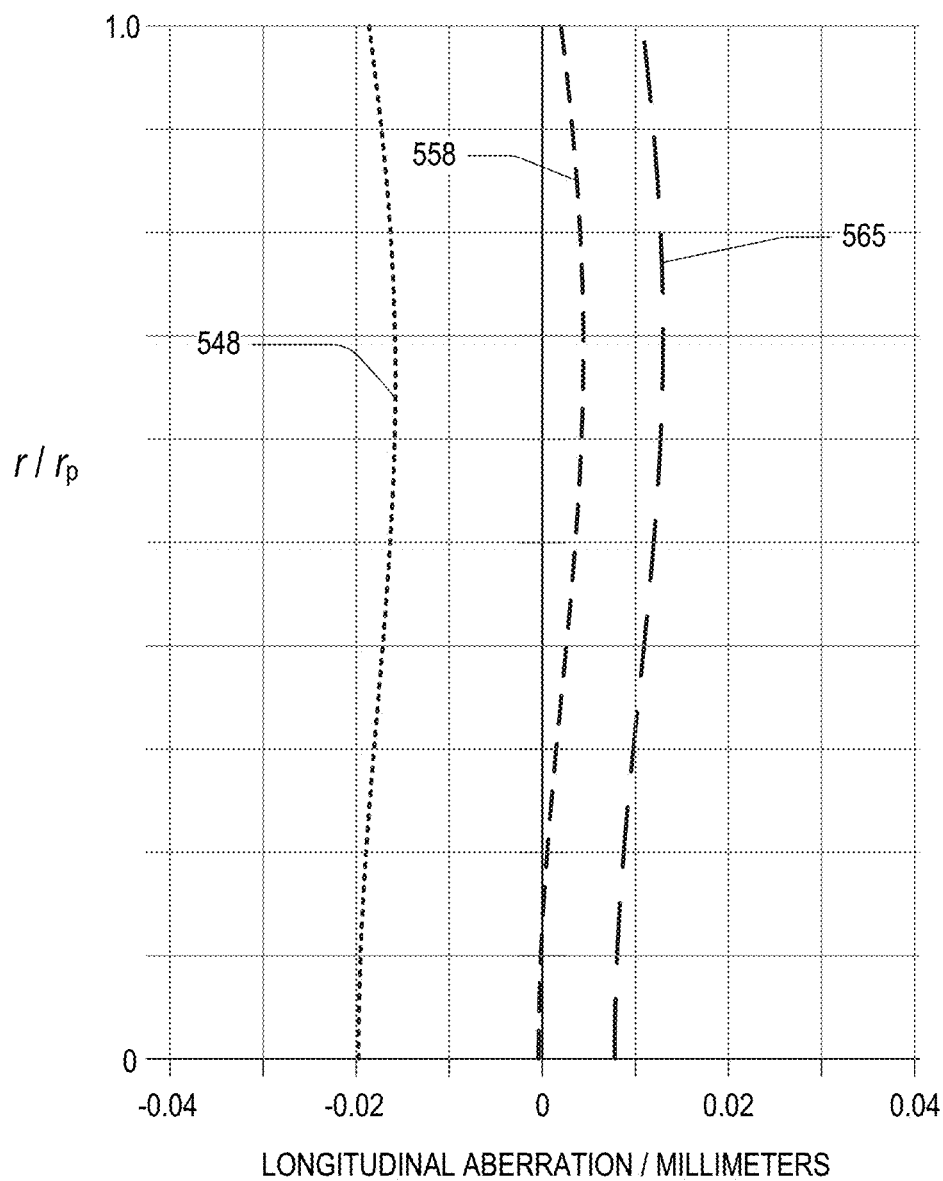
FIG. 5 is a plot of the longitudinal aberration of the compound lens within the imaging system of FIG. 3, according to the parameters of FIG. 4.

FIG. 5 is a plot of the longitudinal aberration of compound lens 300. In FIG. 5, longitudinal aberration is plotted in units of millimeters as a function of normalized radial coordinate $r/r_p$, where $r_p$=0.0807 mm is the maximum entrance pupil radius. Longitudinal aberration curves 548, 558, and 565 are computed at the blue, green, and red Fraunhofer F-, d- and C-spectral lines: $\lambda_F$=486.1 nm, $\lambda_d$=587.6 nm, and $\lambda_C$=656.3 nm respectively.

Figure 6:
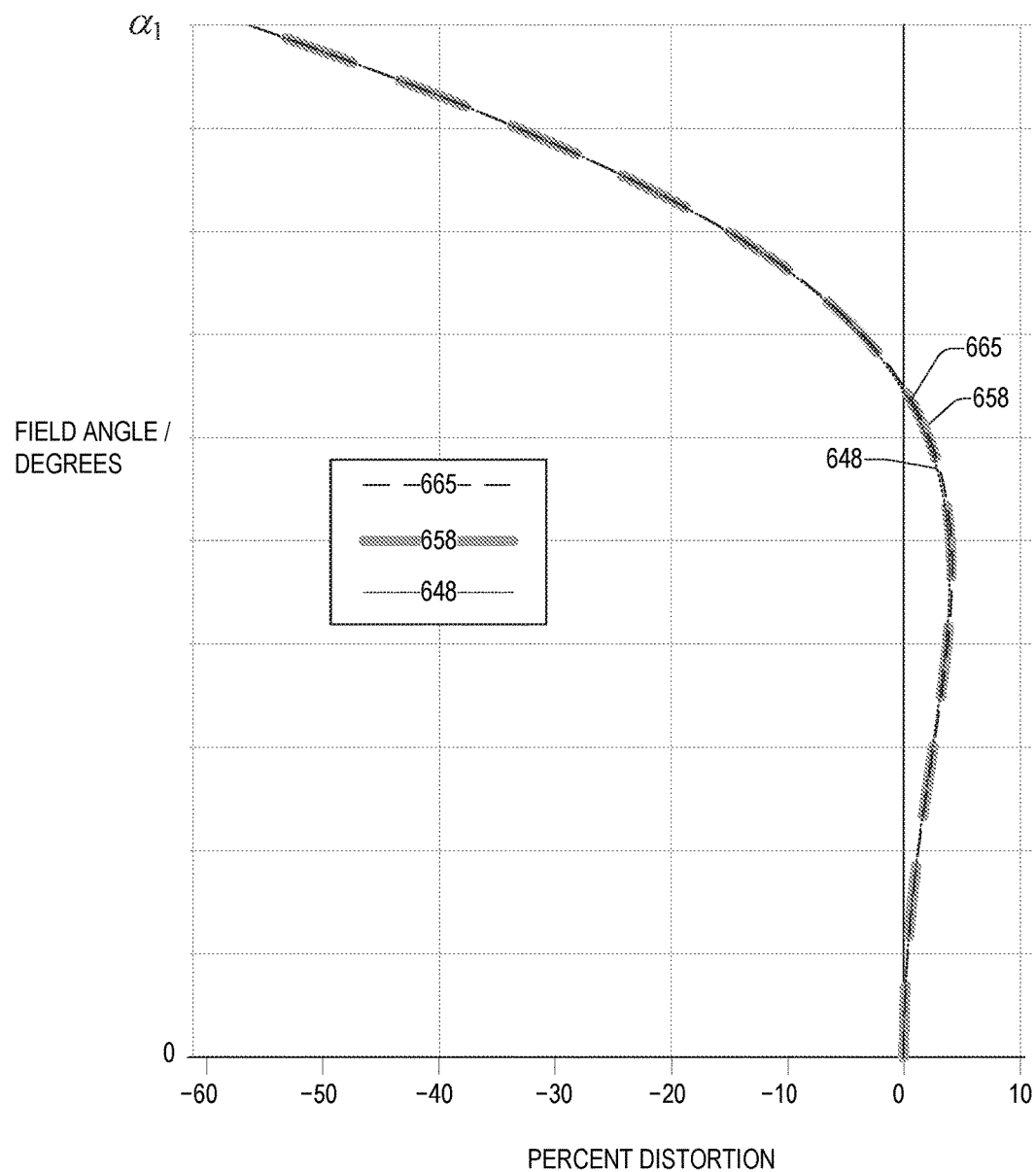
FIG. 6 is a plot of the f-theta distortion of the compound lens within the imaging system of FIG. 3, according to the parameters of FIG. 4.

FIG. 6 is a plot of the f-theta distortion, versus field angle, of compound lens 300. The maximum field angle plotted in FIG. 6 is $\alpha_1$=70.117°, which is half of lens 300's the field of view. Distortion curves 648, 658, and 665 are computed at wavelengths $\lambda_F$, $\lambda_d$, and $\lambda_C$, respectively.

Figure 7:
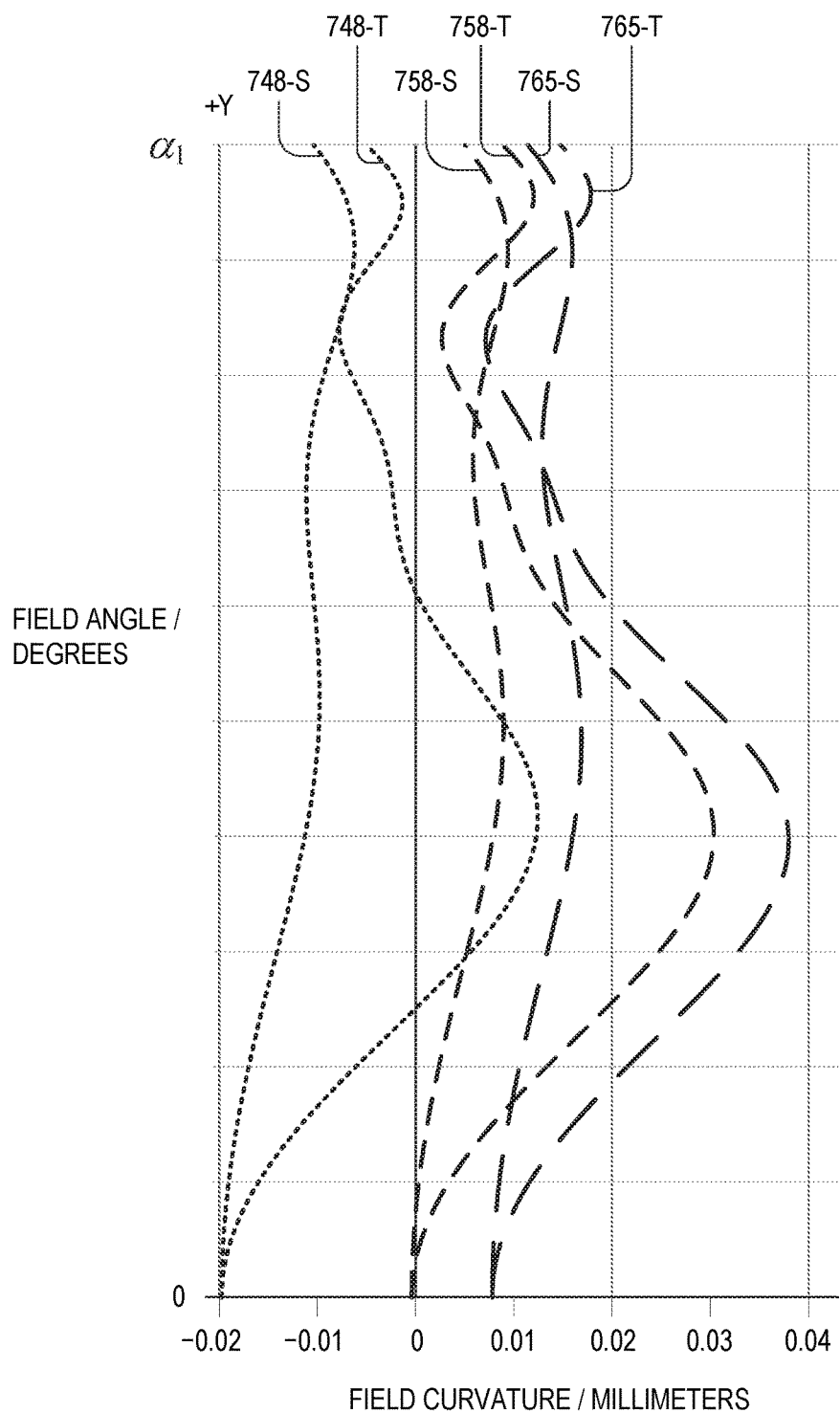
FIG. 7 is a plot of the Petzval field curvature of the compound lens within the imaging system of FIG. 3, according to the parameters of FIG. 4.

FIG. 7 is a plot of the Petzval field curvature, as a function of field angle, of compound lens 300. The field curvature is plotted for field angles between zero and $\alpha_1$. Field curvature 748-S and field curvature 748-T (solid lines) are computed at wavelength $\lambda_F$ in the sagittal and tangential planes, respectively. Field curvature 758-S and field curvature 758-T (short-dashed lines) are computed at wavelength $\lambda_d$ in the sagittal and tangential planes, respectively. Field curvature 768-S and field curvature 768-T (long-dashed lines) correspond to field curvature at wavelength $\lambda_C$ in the sagittal and tangential planes, respectively.

Figure 8:
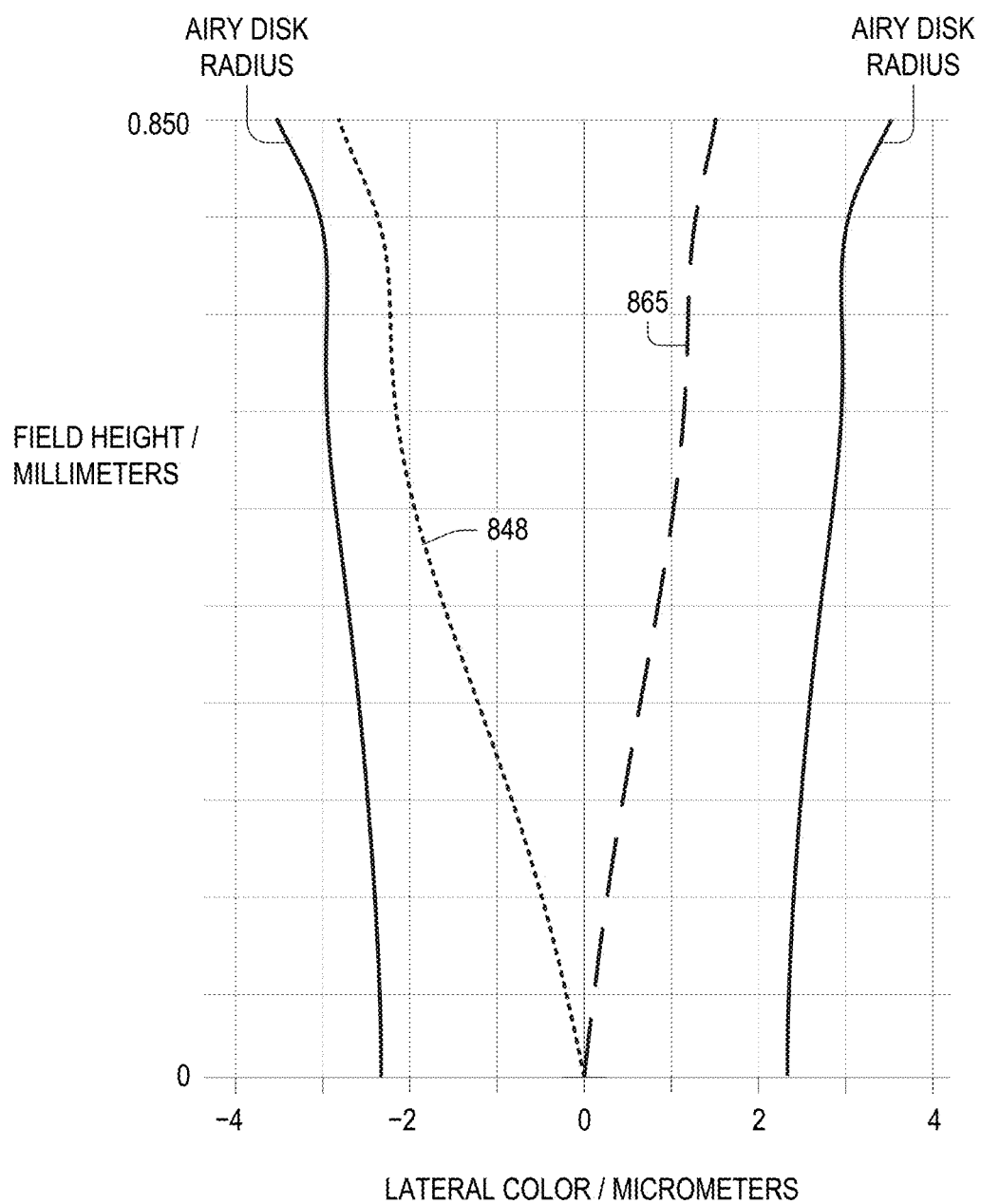
FIG. 8 is a plot of the lateral color error of the compound lens within the imaging system of FIG. 3, according to the parameters of FIG. 4.

FIG. 8 is a plot of the lateral color error, also known as transverse chromatic aberration, versus field height of compound lens 300. Field height ranges from $h_{min}=0$ (on-axis) to $h_{max}=0.850$ mm in image plane 278(1). Lateral color is referenced to $\lambda_d$, and hence the lateral color for $\lambda_d$ is zero for all field heights. Lateral color 848 is computed at wavelength $\lambda_F$. Lateral color 865 is computed at wavelength $\lambda_C$.

Five-Surface Wide Field-of-View Compound Lens, Example 2

Figure 9:
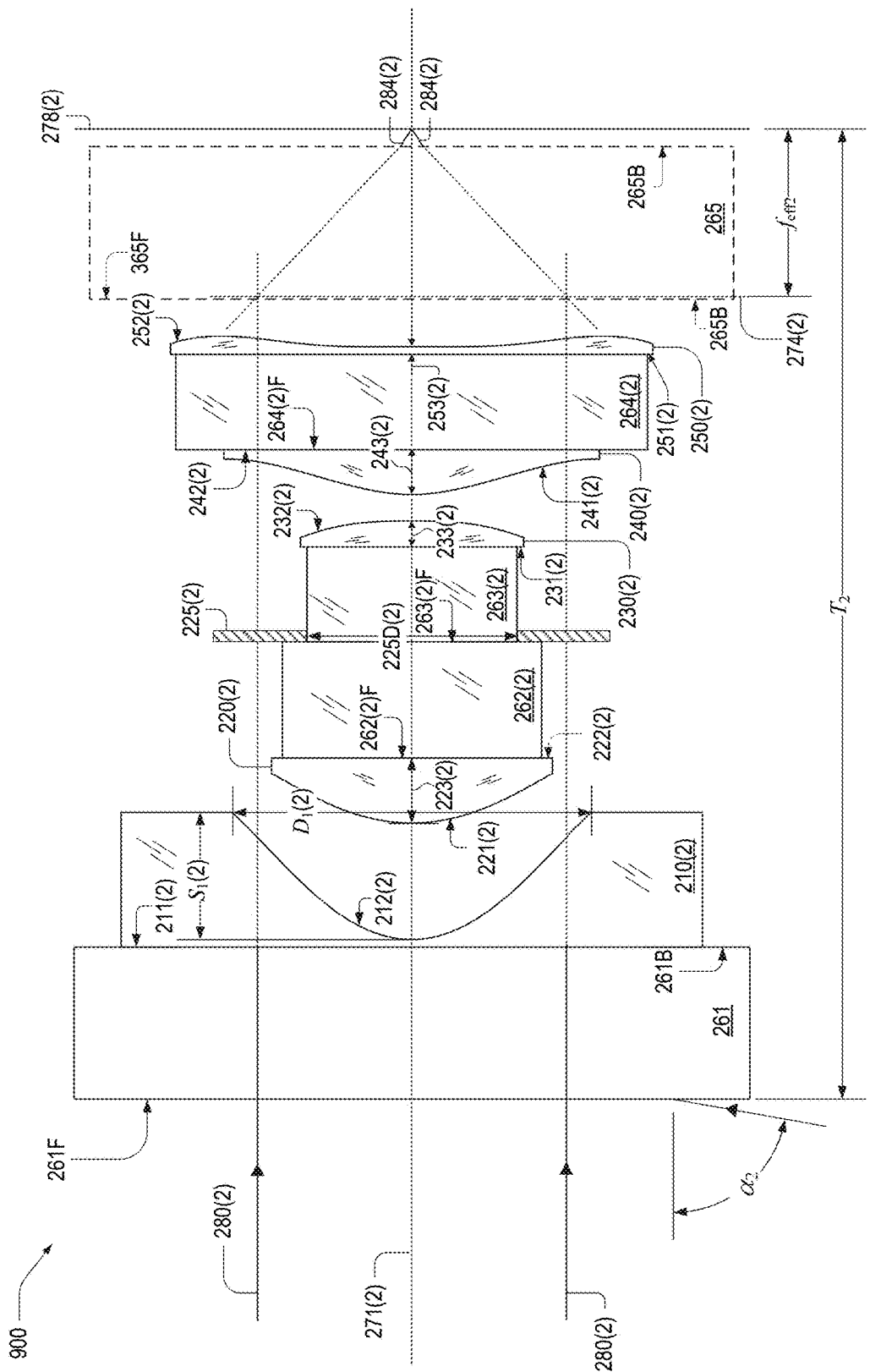
FIG. 9 is a cross-sectional view of an imaging system that includes a second embodiment of the five-surface wide FOV compound lens of FIG. 2.

FIG. 9 is a cross-sectional view of a five-surface wide FOV compound lens 900. Compound lens 900 is an embodiment of five-surface wide FOV compound lens 200. Compound lens 900 includes top substrate 261, substrates 262(2)-264(2), a first lens 210(2), a second lens 220(2), an aperture stop 225(2), a third lens 230(2), a fourth lens 240(2), and a fifth lens 250(2). Lenses 210(2), 220(2), 230(2), and 240(2) have respective planar surfaces 211(2), 222(2), 231(2), 242(2) and 251(2) and respective non-planar surfaces 212(2), 221(2), 232(2), and 241(2). Lens 250(2) has a planar surface 251(2) and a gull-wing surface 252(2). Lenses 210(2), 220(2), 230(2), 240(2), and 250(2) are coaxial with a common optical axis 271(2). Compound lens 900 may also include coverglass 265.

Figure 10:
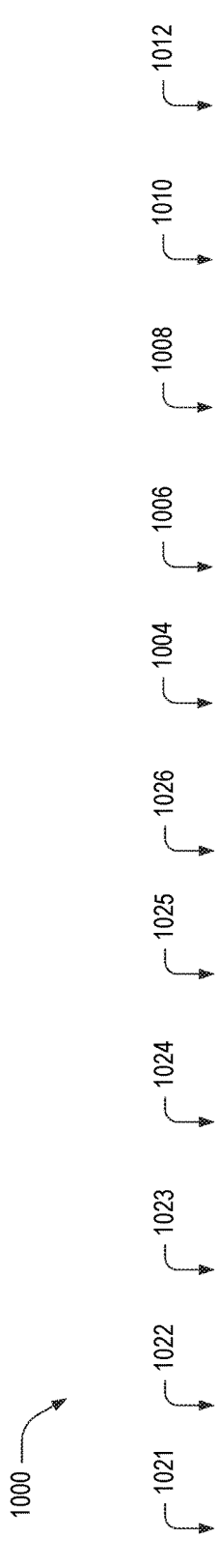
FIG. 10 shows a table of exemplary parameters of the compound lens of FIG. 9.

FIG. 10 shows a table 1000 of exemplary parameters of each surface of compound lens 900 as well as cover glass 265, with which compound lens 900 is configured to cooperate, or which is included in compound lens 900. Table 1000 includes columns 1004, 1006, 1008, 1010, 1012, and 1021-1026. Surface column 1021 denotes surfaces of top substrate 261, substrates 262(2)-264(2), cover glass 265, lenses 210(2), 220(2), 230(2), 240(2), and 250(2) of FIG. 9. Column 1023 includes thickness values, in millimeters, between adjacent surfaces of compound lens 900 on optical axis 271(2). Column 1023 includes center thicknesses of top substrate 261, substrates 262(2)-264(2), cover glass 265, and lenses 210(2), 220(2), 230(2), 240(2), and 250(2). A thickness value in column 1023 in a row denoting a specific surface indicates the on-axis distance between that specific surface and the next surface. Surface 265B is 0.045 mm from image plane 278(2). Aperture stop 225(2) has a diameter 225D(2) equal to 0.204 mm.

It should be appreciated that compound lens 900 need not be configured to cooperate with cover glass 265, in which case parameters of compound lens 900 may be reoptimized to form an image at an image plane absent cover glass 265. Likewise, compound lens 900 may be configured to cooperate with a cover glass 265 of thickness or material different from that specified in table 1000, in which case parameters of compound lens 900 may be reoptimized accordingly to form an image at an image plane.

Surfaces 211(2), 222(2), 231(2), and 242(2) are defined by surface sag $z_{sag}$, shown in Eqn. 1. Column 1022 of FIG. 10 lists $r_c$ values for surfaces 212(2), 222(2), 232(2), 241(2), and 252(2). Parameter k denotes the conic constant, shown in column 1026. Columns 1004, 1006, 1008, 1010, and 1012 contain values of aspheric coefficients $\alpha_4$, $\alpha_6$, $\alpha_8$, $\alpha_{10}$, and $\alpha_{12}$ respectively. The units of quantities in table 1000 are consistent with $z_{sag}$ in Eqn. 1 being expressed in millimeters. Column 1024 lists values material refractive index $n_d$ at free-space wavelength $\lambda_d=587.6$ nm, and column 1025 lists the corresponding Abbe numbers $V_d$.

Compound lens 900 has a working f-number equal to 3.6 and a field of view $2\alpha_2=160$ degrees. At free-space wavelength $\lambda=587.6$ nm, compound lens 300 has an effective focal length $f_{eff2}=0.450$ mm between principal plane 274(2) and image plane 278(2).

First lens 210(2) has a $D_1(2)=0.994$, and a sag $S_1(2) =0.344$ mm, which corresponds to a ratio $D_1(2)/S_1(2)=2.9$. Compound lens 900 has a total track length $T_2=2.549$ mm between surface 261F and image plane 278(2). The ratio of total track length to effective focal length is $T_2/f_{eff2}=5.7$.

Second lens 220(2) and fourth lens 240(2) have focal lengths $F_2$ and $F_4$ respectively, which may be approximated using the lensmaker's equation. Referring to second lens 220(2), object-side surface 221(2) has a 0.4427-mm radius of curvature, and image-side surface 222(2) is has an infinite radius of curvature. Using these radii of curvature, center thickness 223(2), and $n_d=1.61$, the lensmaker's equation yields $F_2 \approx 0.73$ mm. Referring to fourth lens 240(2), object-side surface 241(2) has a 0.4471-mm radius of curvature, and image-side surface 242(2) has an infinite radius of curvature. Using these radii of curvature, center thickness 243(2), and $n_d=1.5110$, the lensmaker's equation yields $F_4 \approx 0.88$ mm. Ratio $F_2/F_4$ is approximately 0.83.

Third lens 230(2) and fifth lens 250(2) have focal lengths $F_3$ and $F_5$ respectively, which may be approximated using the lensmaker's equation. Referring to third lens 230(2), object-side surface 231(2) has an infinite radius of curvature and image-side surface 232(2) has a −3.0168-mm radius of curvature. Using these radii of curvature, center thickness 233(2), and $n_d=1.511$, the lensmaker's equation yields $F_3 \approx 5.90$ mm. Referring to fifth lens 250(2), object-side surface 251(2) has an infinite radius of curvature and image-side surface 252(2) has a −10.2444-mm radius of curvature. Using these radii of curvature, center thickness 253(2), and $n_d=1.52$, the lensmaker's equation yields $F_5 \approx 19.70$ mm. Ratio $|F_3/F_5|$ is approximately 0.30.

FIGS. 11-14 are plots of longitudinal aberration, f-theta distortion, field curvature, and lateral color, respectively, of compound lens 900 as computed by Zemax®.

Figure 11:
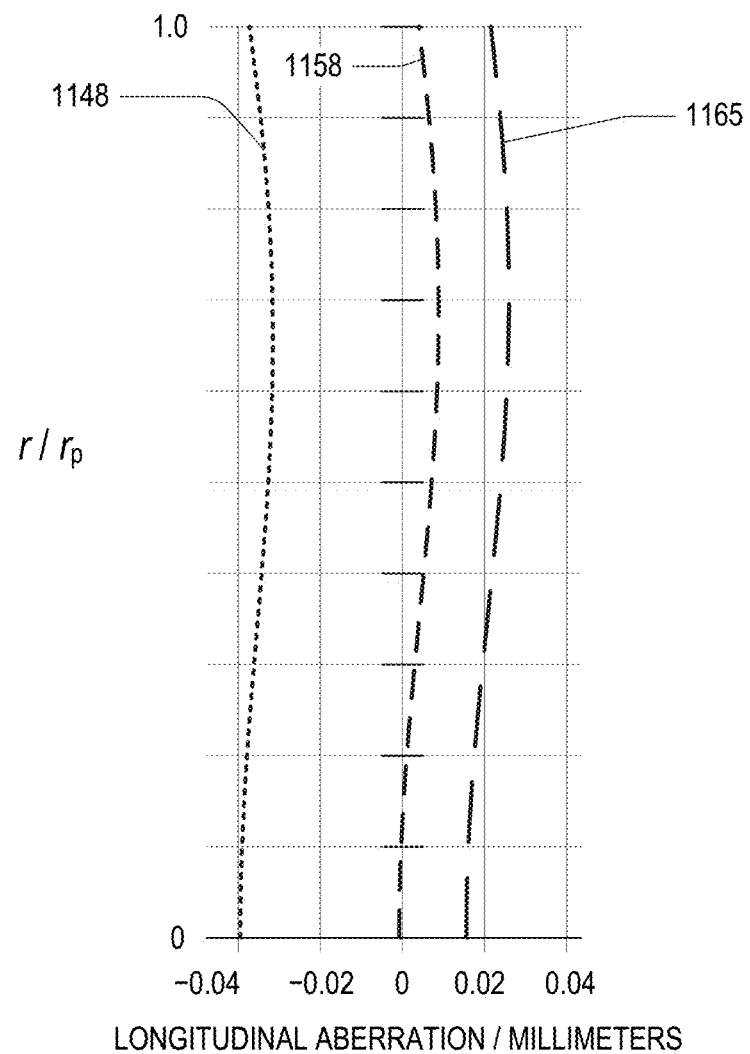
FIG. 11 is a plot of the longitudinal aberration of the compound lens within the imaging system of FIG. 9, according to the parameters of FIG. 10.

FIG. 11 is a plot of the longitudinal aberration of compound lens 900. In FIG. 11, longitudinal aberration is plotted in units of millimeters as a function of normalized radial coordinate $r/r_p$, where $r_p=0.0807$ mm is the maximum entrance pupil radius. Longitudinal aberration curves 1148, 1158, and 1165 are computed at $\lambda_F$, $\lambda_d$, and $\lambda_C$ respectively.

Figure 12:
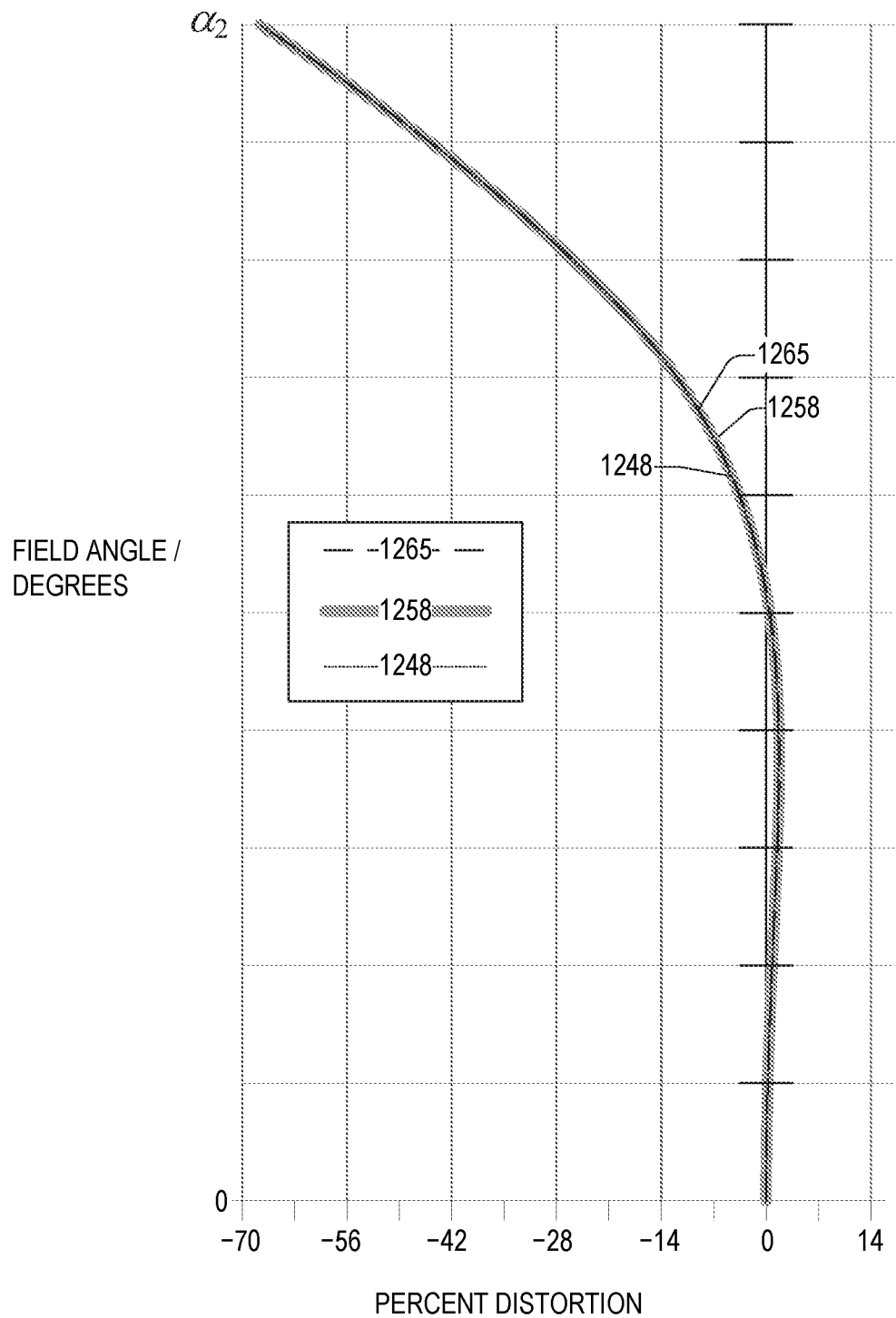
FIG. 12 is a plot of the f-theta distortion of the compound lens within the imaging system of FIG. 9, according to the parameters of FIG. 10.
Figure 13:
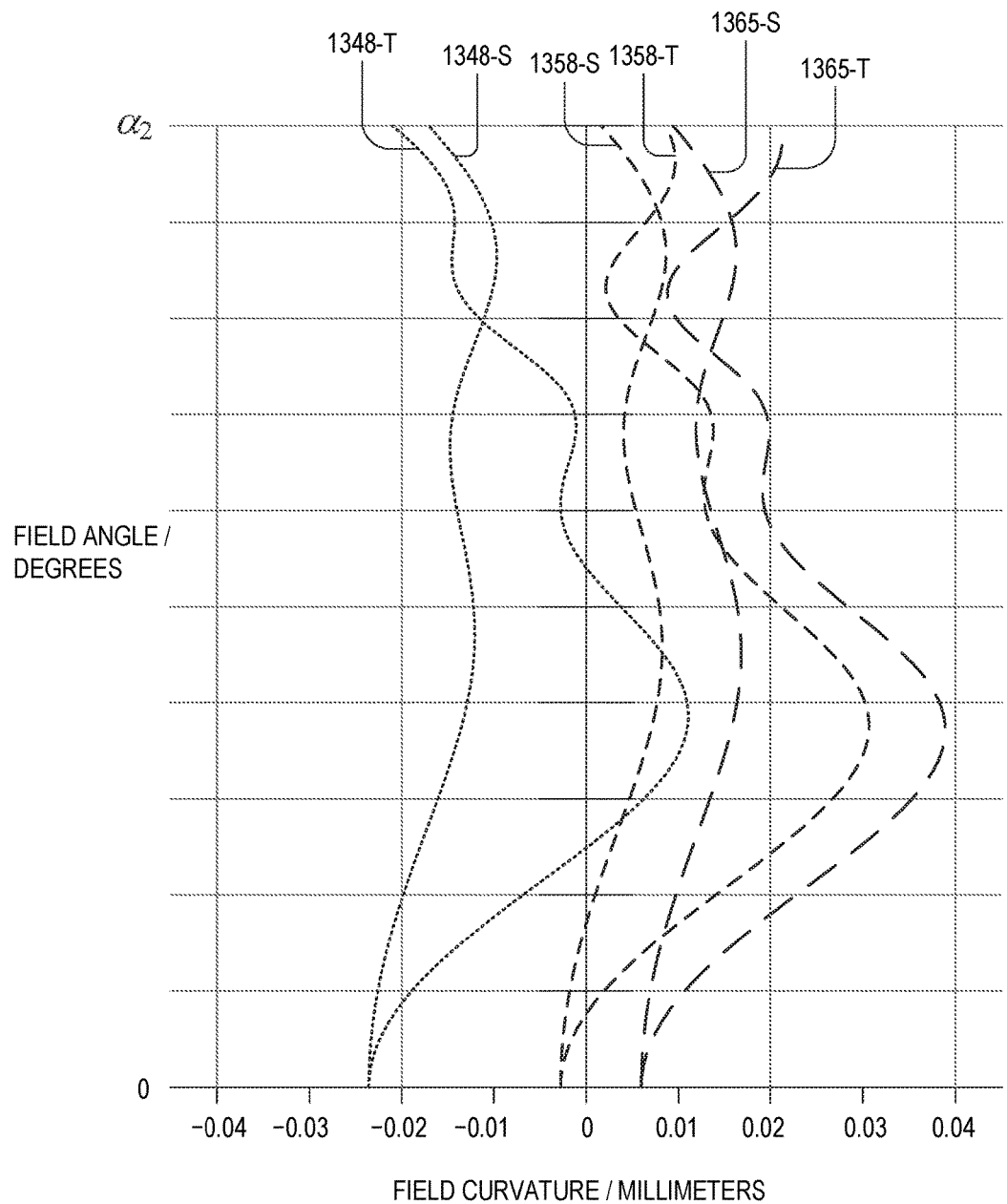
FIG. 13 is a plot of the Petzval field curvature of the compound lens within the imaging system of FIG. 9, according to the parameters of FIG. 10.

FIG. 12 is a plot of the f-theta distortion, versus field angle, of compound lens 900. The maximum field angle plotted in FIG. 13 is $\alpha_2=80.008°$, which is half of lens 900's the field of view. Distortion curves 1248, 1258, and 1265 are computed at wavelengths $\lambda_F$, $\lambda_d$, and $\lambda_C$, respectively.

FIG. 13 is a plot of the Petzval field curvature, as a function of field angle, of compound lens 900. The field curvature is plotted for field angles between zero and $\alpha_2$. Field curvature 1348-S and field curvature 1348-T (solid lines) are computed at wavelength $\lambda_F$ in the sagittal and tangential planes, respectively. Field curvature 1358-S and field curvature 1358-T (short-dashed lines) are computed at wavelength $\lambda_d$ in the sagittal and tangential planes, respectively. Field curvature 1365-S and field curvature 1365-T (long-dashed lines) correspond to field curvature at wavelength $\lambda_C$ in the sagittal and tangential planes, respectively.

Figure 14:
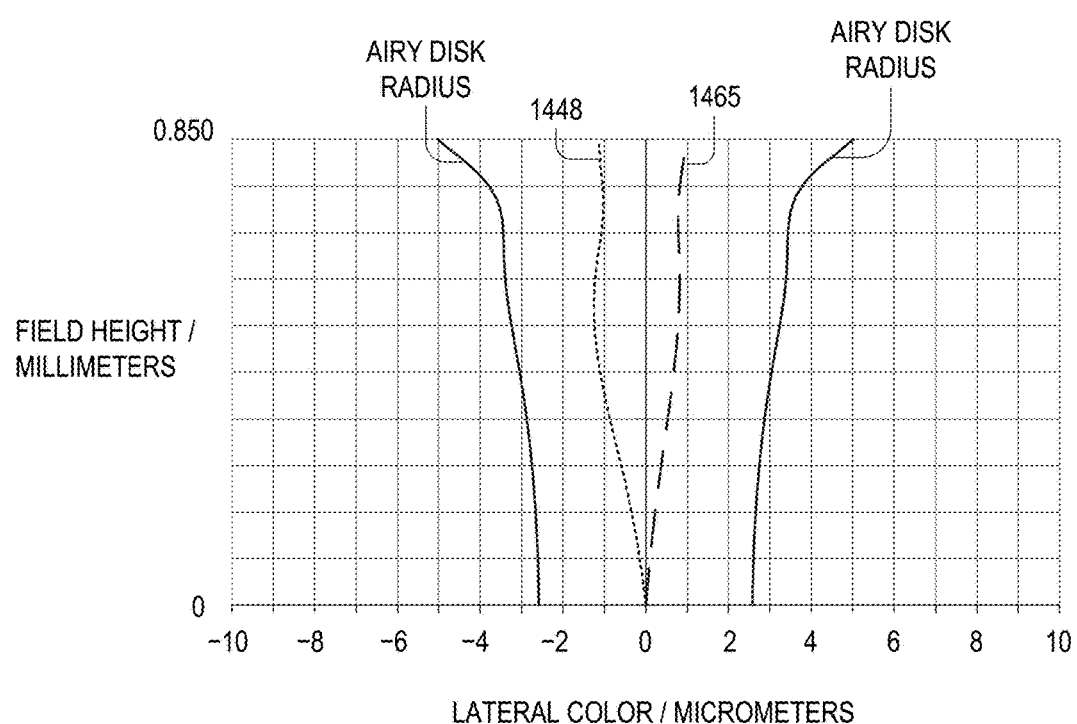
FIG. 14 is a plot of the lateral color error of the compound lens within the imaging system of FIG. 9, according to the parameters of FIG. 10.

FIG. 14 is a plot of the lateral color error, also known as transverse chromatic aberration, versus field height of compound lens 900. Field height ranges from $h_{min}=0$ (on-axis) to $h_{max}=0.850$ mm in image plane 278(2). Lateral color is referenced to $\lambda_d$, and hence the lateral color for $\lambda_d$ is zero for all field heights. Lateral color 1448 is computed at wavelength $\lambda_F$. Lateral color 1465 is computed at wavelength $\lambda_C$.

Figure 15:
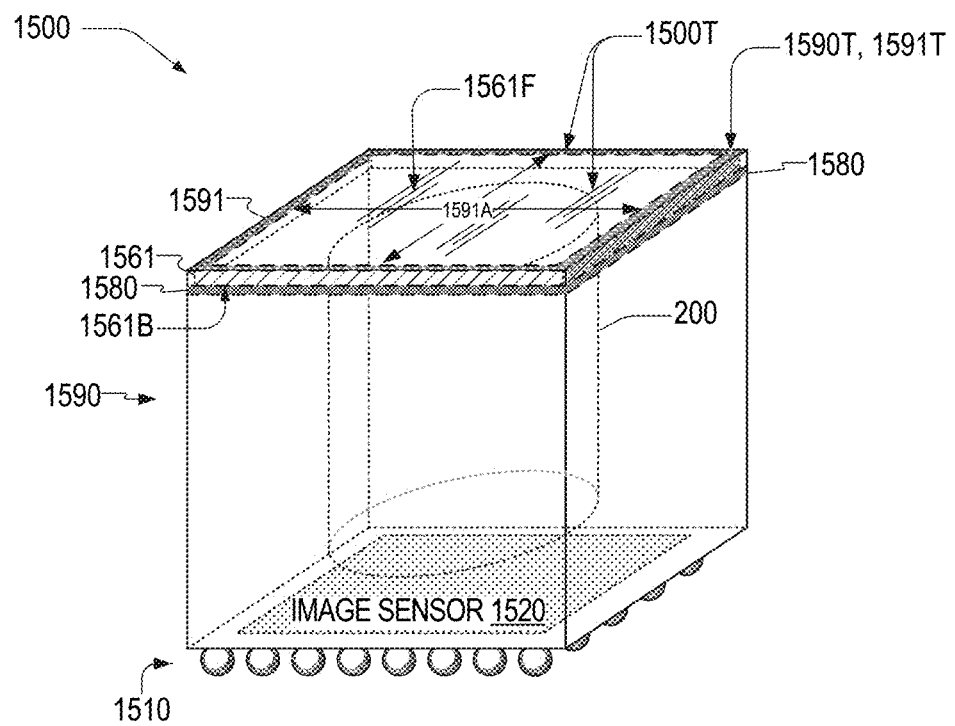
FIG. 15 illustrates a camera module that includes the five-surface wide FOV compound lenses of FIG. 2, in an embodiment.

FIG. 15 is a perspective view of a camera module 1500 that includes five-surface wide FOV compound lens 200. Camera module 1500 also includes a housing 1590, an image sensor 1520, a top window 1561, and optionally a ball-grid array 1510 electrically connected to image sensor 1520. Top window 1561 is an example of top substrate 261, and has a top surface 1561F and a bottom surface 1561B. Top surface 1561F is an example of surface 261F, and hence may be planar. Housing 1590 is for example formed of metal or plastic. Image sensor 1520 is for example a complementary metal-oxide-semiconductor (CMOS) image sensor.

Camera module 1500 has a top surface 1500T, at least part of which includes top surface 1561F. Top window 1561 may be bonded to housing 1590. For example, housing 1590 may include a top ridge 1591 having a bottom surface, facing image sensor 1520, to which top surface 1561F may be bonded. Top ridge 1591 has a top surface 1591T corresponding to a top exterior surface 1590T of housing 1590, such that top surface 1500T includes both top exterior surface 1590T and the region of top surface 1561F within an aperture 1591A formed by top ridge 1591. Alternatively, housing 1590 includes a ridge 1580 therein to which top window 1561 may be bonded, i.e., such that bottom surface 1561B is on ridge 1580.

Top window 1561 protects lens 200 and provides camera module 1500 with robust top surface (surface 1561F) having material hardness (e.g., scratch hardness) that exceeds that of UV-curable epoxy, which may constitute component lenses of lens 200 and can withstand processes of sterilization and also hermetically seal camera module 1500. Camera module 1500 may be hermetically sealed, for example, for use in medical applications such as endoscopy.

Combinations of Features:

Features described above as well as those claimed below may be combined in various ways without departing from the scope hereof. The following examples illustrate some possible, non-limiting combinations:

(A1) A five-surface wide FOV compound lens includes: a first lens and, in order of increasing distance therefrom and on a same side thereof, a second lens, a third lens, a fourth lens, and a fifth lens. The first, second, third, fourth, and fifth lens are coaxial. The compound lens also includes (i) a first biplanar substrate between the second lens and the third lens and (ii) a second biplanar substrate between the fourth lens and the fifth lens. The first lens is a negative lens. The second, third, and fourth lenses are each positive lenses. The fifth lens is a plano-gull-wing lens.

(A2) In the lens denoted by (A1), the first lens may have a first Abbe number that exceeds a second Abbe number of the second lens.

(A3) In the lens denoted by (A2), the first Abbe number may exceed 48 and the second Abbe number may be less than 35.

(A4) In any lens denoted by one of (A1) through (A3) in which the second lens has a focal length $F_2$, the third lens has a focal length $F_3$, the fourth lens has a focal length $F_4$, and the fifth lens has a focal length $F_5$, the ratio $F_2/F_4$ may satisfy $0.65<F_2/F_4<0.95$, and the absolute value of ratio $F_3/F_5$ may satisfy $0.2<|F_3/F_5|<0.6$.

(A5) In any lens denoted by one of (A1) through (A4), in which the first lens has a diameter $D_1$, and a sag $S_1$, the ratio $D_1/S_1$ may satisfy $2.5<D_1/S_1<3.2$.

(A6) In any lens denoted by one of (A1) through (A5), the first lens may have a planar surface and a concave surface opposite the planar surface and facing the second lens.

(A7) Any lens denoted by one of (A1) through (A6), may have an effective focal length between 0.40 millimeters and 0.55 millimeters.

(A8) Any lens denoted by one of (A1) through (A7), may have an f-number between 3.0 and 4.0.

(A9) Any lens denoted by one of (A1) through (A8) may further include a top substrate having a planar surface adjoining a first planar surface of the first lens, in which the first lens is between the top substrate and the second lens.

(A10) Any lens denoted by one of (A1) through (A9) may have a field of view exceeding 155 degrees.

(A11) Any lens denoted by one of (A1) through (A10) may have an effective focal length $f_{eff}$ such that the compound lens forms an image at an image plane located a distance T from a front surface of the top substrate opposite the first lens, and the ratio $T/f_{eff}$ may satisfy $5.0<T/f_{eff}<5.8$.

(A12) A camera module includes a housing and any lens denoted by one of (A9) through (A11). The camera module has a top substrate, formed of glass, that has a second planar surface opposite the planar surface, at least part of the second planar surface being an exterior surface of the camera module.

(A13) In the camera module denoted by (A12), the top substrate may provide part of a hermetic seal for the camera module.

Changes may be made in the above methods and systems without departing from the scope hereof. It should thus be noted that the matter contained in the above description or shown in the accompanying drawings should be interpreted as illustrative and not in a limiting sense. The following claims are intended to cover all generic and specific features described herein, as well as all statements of the scope of the present method and system, which, as a matter of language, might be said to fall there between.

What is claimed is:

1. A five-surface wide field-of-view (FOV) compound lens comprising:
   five coaxially aligned lenses including, in order, a negative first lens, a positive second lens, a positive third lens, a positive fourth lens, and a plano-gull wing fifth lens;
   a first biplanar substrate between the second lens and the third lens; and
   a second biplanar substrate between the fourth lens and the fifth lens, the first lens having an Abbe number that exceeds an Abbe number of the second lens.

2. The compound lens of claim 1, the Abbe number of the first lens exceeding 48, the Abbe number of the second lens being less than 35.

3. The compound lens of claim 1 the second lens having a focal length $F_2$, the fourth lens having a focal length $F_4$ such that $0.65<F_2/F_4<0.95$.

4. The compound lens of claim 1, the third lens having a focal length $F_3$, the fifth lens having a focal length $F_5$ such that $0.2<|F_3/F_5|<0.6$.

5. The compound lens of claim 1, the first lens having a diameter $D_1$, and a sag $S_1$ such that $2.5<D_1/S_1<3.2$.

6. The compound lens of claim 1, the first lens having a planar surface and a concave surface opposite the planar surface and facing the second lens.

7. The compound lens of claim 1, having an effective focal length between 0.40 millimeters and 0.55 millimeters.

8. The compound lens of claim 7, having an f-number between 3.0 and 4.0.

9. The compound lens of claim 1, further comprising a top substrate having a planar surface adjoining a first planar surface of the first lens, the first lens being between the top substrate and the second lens.

10. The compound lens of claim 9, having an effective focal length $f_{eff}$ such that (i) the compound lens forms an image at an image plane located a distance T from a front surface of the top substrate opposite the first lens, and (ii) $5.0<T/f_{eff}<5.8$.

11. A camera module comprising a housing and the compound lens of claim 9, the top substrate being formed of glass having a second planar surface opposite the planar surface, at least part of the second planar surface being an exterior surface of the camera module.

12. The camera module of claim 11, the top substrate providing part of a hermetic seal for the camera module.

13. The compound lens of claim 1, having a field of view exceeding 155 degrees.

14. The compound lens of claim 1, the second and third lenses being disposed on the first biplanar substrate, the fourth and fifth lenses being disposed on the second biplanar substrate.

15. A five-surface wide field-of-view (FOV) compound lens comprising:
   five coaxially aligned lenses including, in order, a negative first lens, a positive second lens, a positive third lens, a positive fourth lens, and a plano-gull wing fifth lens;
   a first biplanar substrate between the second lens and the third lens; and
   a second biplanar substrate between the fourth lens and the fifth lens,
   the second lens having a focal length $F_2$, the fourth lens having a focal length $F_4$, the ratio $F_2/F_4$ satisfying $0.65<F_2/F_4<0.95$.

16. The compound lens of claim 15, the first lens having a first Abbe number that exceeds a second Abbe number of the second lens.

17. The compound lens of claim 16, the first Abbe number exceeding 48, the second Abbe number being less than 35.

18. The compound lens of claim 15, the third lens having a focal length $F_3$, the fifth lens having a focal length $F_5$ such that $0.2<|F_3/F_5|<0.6$.

19. The compound lens of claim 15, the first lens having a diameter has a diameter $D_1$, and a sag $S_1$ such that $2.5<D_1/S_1<3.2$.

20. The compound lens of claim 15, the first lens having opposite facing planar surface and concave surface, the concave surface facing the second lens.

21. The compound lens of claim 15, further comprising a top substrate having a planar surface adjoining a first planar surface of the first lens, the first lens being between the top substrate and the second lens.

22. The compound lens of claim 21, having an effective focal length $f_{eff}$ such that the compound lens forms an image at an image plane located a distance T from a front surface of the top substrate opposite the first lens such that $5.0<T/f_{eff}<5.8$.

* * * * *